Figure 1:
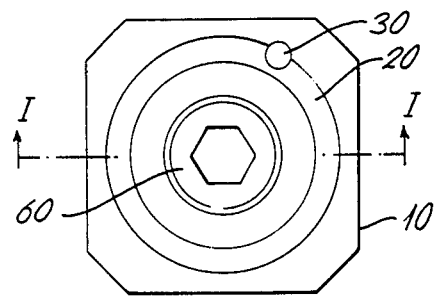

United States Patent [19]

Evans

[11] Patent Number: 4,693,240
[45] Date of Patent: Sep. 15, 1987

[54] ORTHOPAEDIC FRACTURE FIXATION APPARATUS

[75] Inventor: Mervyn Evans, Kidlington, England

[73] Assignee: National Research Development Corporation, London, England

[21] Appl. No.: 722,387

[22] Filed: Apr. 12, 1985

[30] Foreign Application Priority Data

Apr. 12, 1984 [GB] United Kingdom ............ 8409564

[51] Int. Cl.$^4$ .............................................. A61F 5/04
[52] U.S. Cl. ........................... 128/92 Z; 128/92 ZW; 403/55; 403/90; 403/362
[58] Field of Search ............ 128/92 R, 92 Z, 92 VZ, 128/92 ZZ, 92 ZK, 92 ZY, 92 ZW, 92 Y, 84 B; 403/55, 84, 90, 362

[56] References Cited

U.S. PATENT DOCUMENTS

| | | | |
|---|---|---|---|
| 169,383 | 11/1875 | Starr | 403/90 |
| 490,541 | 1/1903 | Case | 403/90 |
| 2,014,638 | 9/1935 | Scofield | 128/92 ZW |
| 2,346,346 | 4/1944 | Anderson | 128/92 Z |
| 2,391,537 | 12/1945 | Anderson | 128/92 Z |
| 4,127,119 | 11/1978 | Kronner | 128/92 Z |
| 4,265,561 | 5/1981 | Heckele | 403/90 |
| 4,271,832 | 6/1981 | Evans et al. | 128/92 Z |
| 4,393,868 | 7/1983 | Teague | 128/92 ZW |
| 4,456,004 | 6/1984 | Kenny | 128/92 ZW |
| 4,541,422 | 9/1985 | de Zbikowski | 128/92 ZW |
| 4,579,009 | 4/1986 | Carmichael et al. | 403/90 |

FOREIGN PATENT DOCUMENTS

| | | | |
|---|---|---|---|
| 392266 | 7/1924 | Fed. Rep. of Germany | 403/90 |
| 2029702B | 3/1980 | United Kingdom . | |
| 2029702A | 3/1980 | United Kingdom . | |
| 2031731A | 4/1980 | United Kingdom . | |

*Primary Examiner*—C. Fred Rosenbaum
*Assistant Examiner*—Mario Costantine
*Attorney, Agent, or Firm*—Cushman, Darby & Cushman

[57] ABSTRACT

A bone pin clamp for external fracture fixation apparatus comprises rotation, slide and housing elements (240, 220, 210) nested one within the next, each such element being apertured to receive a pin (100) therethrough, and the rotation and slide elements respectively affording pin adjustment in azimuth and zenith, and in height, relative to the housing element, and a locking mechanism (60, 80, 170) including a common actuator member (60) operable simultaneously to lock the pin and rotation and slide elements in the housing element. In a preferred form the housing element serves as a cylinder with the slide element as a keyed piston therein, and the rotation element is a disc located between a screw (60) and annular thrust members (80, 170) engaged in the piston, the piston and disc being split respectively to lock by expansion and compaction under screw action towards the thrust members.

5 Claims, 21 Drawing Figures

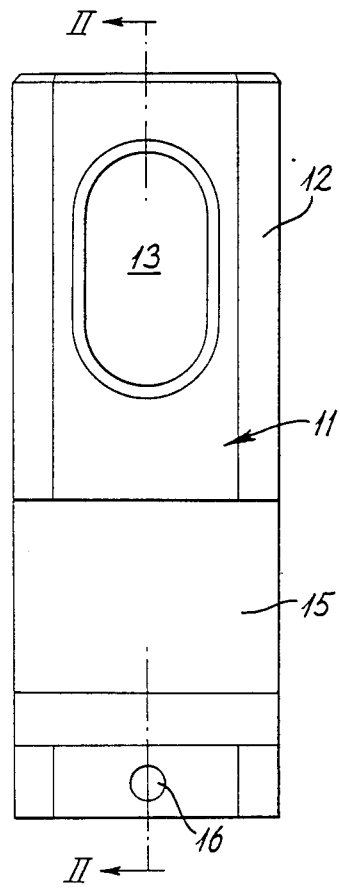
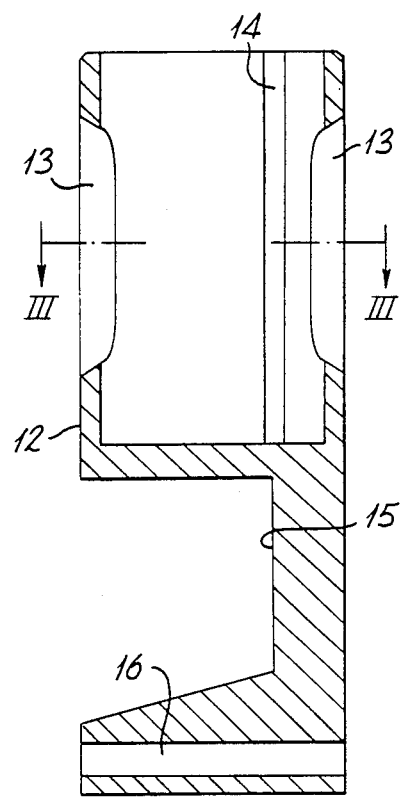
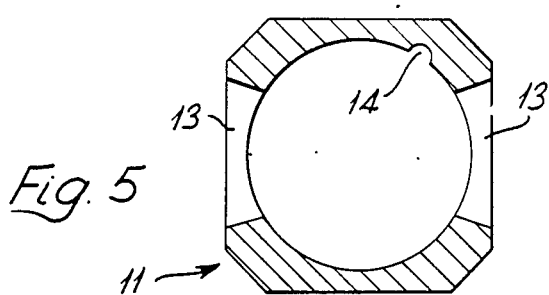

ORTHOPAEDIC FRACTURE FIXATION APPARATUS

This invention concerns orthopaedic fracture fixation apparatus and more particularly such apparatus of the so-called "external" kind.

This external kind of apparatus is, in use, located outside a patient's body and is variably connectable with the fragments of a fractured bone by way of bone pins to form a support frame which holds the fragments in a desired positional relationship for the purposes of re-union. Generally speaking such apparatus involves one or more support members of bar or equivalent form, and clamps to interconnect the bone pins therewith, the clamps being positionally adjustable relative to the members and/or pins.

While most commonly used in relation to fractures resulting from injury, apparatus of the kind in question is also applicable to the support of bone divided deliberately for the purposes of lengthening a bone or fusing two neighbouring bones at a joint.

A particular form of external fracture fixation is described in Pat. No. 4,271,832 which is beneficial by its use of clamps each affording adjustment of a pin in azimuth, zenith and height relative to an associated support, while being lockable by a common mechanism. The distinctive basis for this form of clamp is a hollow body through which a pin can be passed, the body housing a plurality of ball bearings and co-acting with pressure-applying means operable to clamp the pin by immobilising the balls therearound in any one position of the pin among a range through which it is otherwise movable.

This particular apparatus has proved successful by virtue of adoption for commercial manufacture and routine clinical usage, but it is considered open to improvement. More specifically the clamp of this apparatus can be viewed as presenting some undesirable constraints by virtue of its reliance on a plurality of ball bearings, and an object of the present invention is the provision of an alternative form of clamp of simplified structure but affording similar operational characteristics.

Accordingly there is provided, in or for external orthopaedic fracture fixation apparatus, a clamp comprising rotation, slide and housing elements nested one within the next, each said element being apertured to receive a pin therethrough, and said rotation and slide elements respectively affording adjustment of said pin in azimuth and zenith on the one hand and height on the other hand relative to said housing element, and a locking mechanism including a common actuator member operable simultaneously to lock said pin and said rotation and slide elements in said housing element.

In a preferred form of this clamp the housing element includes a hollowed body serving as a cylinder in which the slide element is reciprocable as a piston keyed against rotation, the housing and slide elements each having a pair of apertures which are correspondingly diametrally opposed for passage of the pin therethrough, and the housing element apertures being elongated relative to the slide element apertures in the direction of reciprocation of the slide element.

In this last form the locking mechanism preferably includes a screw as said actuator member and a thrust member engaged in said slide element in opposed locations about said rotation element, the slide element being of split form adjacent said thrust member to expand and lock within said housing element upon threaded intrusion of said screw into said slide element, said screw acting on said thrust member by way of said rotation element simultaneously to lock the latter.

Also in this last form the rotation element can be of single-part or multi-part construction.

The present preference is for multi-part construction, there suitably being two parts respectively affording pin adjustment in azimuth and zenith and, again, being nested one within the other.

As presently developed the proposed clamp is intended for use in similar manner to that of the above-mentioned Patient. Thus there will be a plurality of like clamps longitudinally adjustably securable along a common support bar, each clamp having its slide element, rotation element and locking mechanism located at one end of its housing element, with the last element being adapted at its opposite end for slidably adjustable securement on the support.

Figure 2:
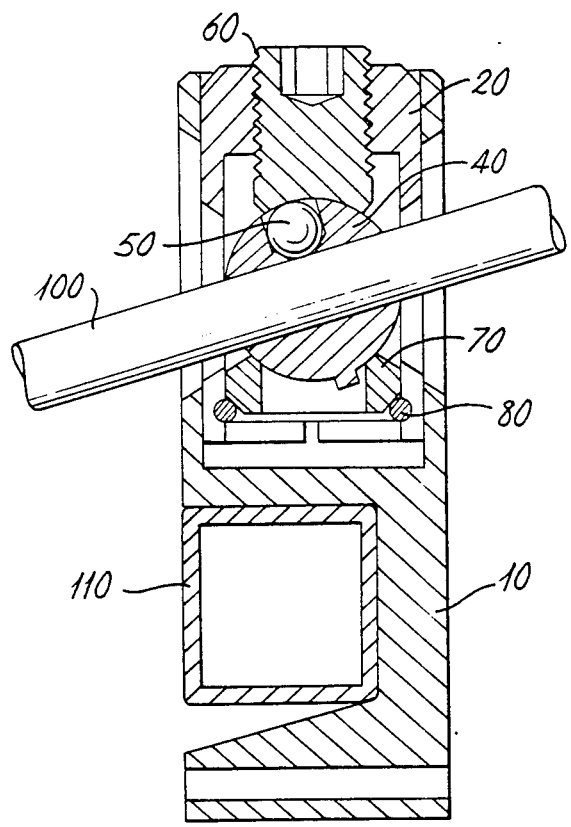
Figure 6:
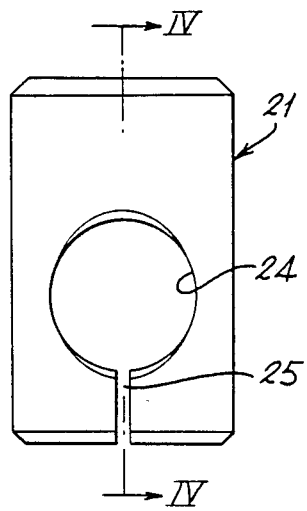
Figure 7:
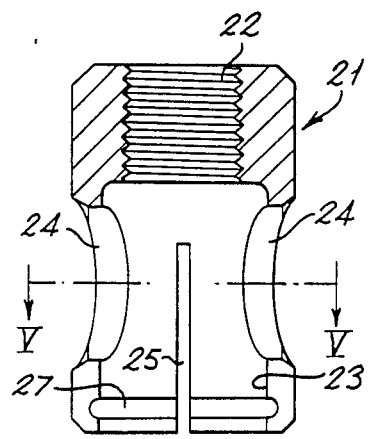
Figure 8:
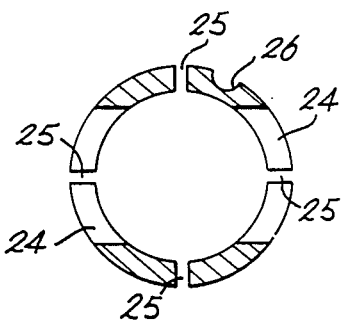
Figure 9:
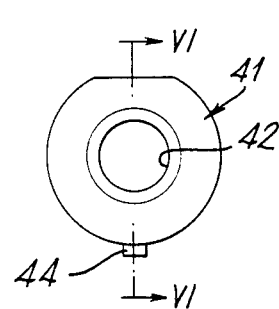
Figure 10:
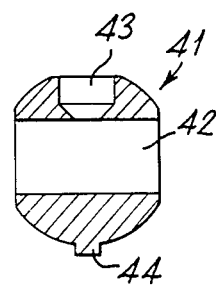
Figure 11:
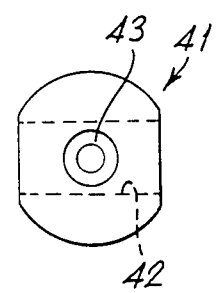
Figure 12:
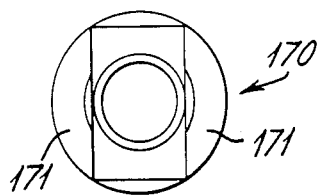
Figure 13:
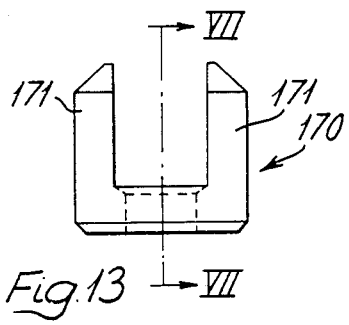
Figure 14:
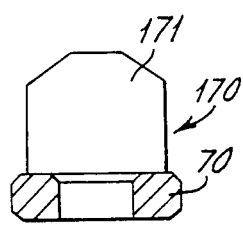
Figure 15:
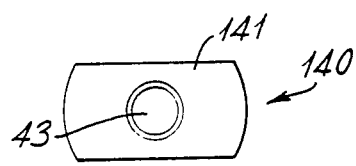
Figure 17:
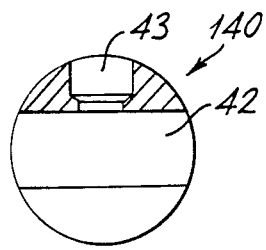
Figure 16:
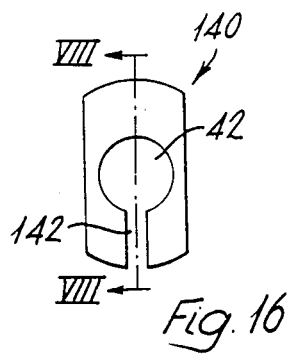
Figure 18:
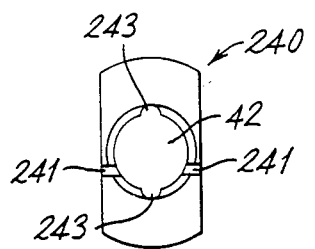
Figure 19:
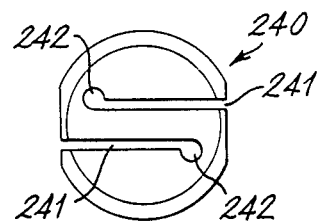

However, it is to be understood that variation is possible within the invention as so far described and this can be appreciated from the following more detailed description of the invention, given by way of example, with reference to the accompanying drawings, in which:

FIGS. 1 and 2 respectively illustrate in plan view and sectional view taken at I—I an initially developed form of clamp according to the invention, FIGS. 3, 4 and 5 respectively illustrate in front elevation and sectional views taken at II—II and III—III the housing element of this clamp, FIGS. 6, 7 and 8 similarly illustrate, with sections taken at IV—IV and V—V, the slide element of this clamp, FIGS. 9, 10 and 11 respectively illustrate in front elevation, sectional view taken at VI—VI, and plan view, the rotation element of this clamp, FIGS. 12, 13 and 14 respectively illustrate in plan view, side elevaion, and a sectional view taken at VII-—VII, one part of a subsequently developed form of rotation element of two-part construction for this clamp, FIGS. 15, 16 and 17 respectively illustate in plan view, side elevation, and sectional view taken at VIII-—VIII, the other part of this subsequent rotation element, FIGS. 18 and 19 respectively illustrate in side and front elevations a preferred further development of the part of FIGS. 15 to 17, and FIGS. 20 and 21 respectively illustrate in corresponding manner to FIGS. 1 and 2 a presently preferred clamp incorporating the part of FIGS. 18 and 19 and modified housing and slide elements.

The clamp of FIGS. 1 and 2 comprises a housing element 10, a slide element 20, a key 30, a rotation element 40, a roller 50, a screw 60, a thrust ring 70, and a locking ring 80. Also shown in FIG. 2 are an associated bone pin 100 and support member 110.

In describing overall this assembly, reference is also made to FIGS 3 to 5, 6 to 7 and 9 to 11 which respectively illustrate the housing, slide and rotation elements 10, 20 and 40 in more detail.

The housing element 10 (FIGS 3 to 5) comprises a generally rectangular body 11 having substantially square cross-sectional shape over a length greater than the transverse dimensions. One end portion 12 of this body is axially bored from its free end to a cylindrical form, and one opposed pair of side faces are formed with like apertures 13 therethrough, these apertures being elongated axially of the body. Also the internal surface of this bored portion is formed with an axial groove 14 over its length. The other end portion of the body 11 is to be slidably adjustably securable along the support member 110 which is shown as a hollowed square bar. The body is shown with a recess 15 across its width over one of the apertured side faces, and also a bolt hole 16, for securement to the bar generally in accordance with the abovementioned Patent, but it can be alternatively adapted for securement to a support member in any other suitable manner.

The slide element 20 (FIGS. 6 to 8) comprises a circular cylindrical body 21 dimensioned to engage in the bore of the housing element 10 in the manner of a piston. The body 21 is formed axially with a threaded bore 22 from one end and a counterbore 23 from the other end. The counterbored end is formed with a pair of opposed like apertures 24 and four axial slots 25 from its free end. The slots 25 are uniformly distributed circumferentially of the element and extend part way along the counterbored end with two of the slots respectively communicating with the apertures 24. The element also has an axial groove 26 extending over the length of its external surface, and the counterbored end also has a circumferential groove 27 formed in its internal surface adjacent the mouth of the counterbore.

In assembly of the clamp, the slide element 20 is engaged, with its threaded bore outermost, in the cylindrical end portion 12 of the housing element 10. More specifically, this engagement is effected with the respective grooves 14 and 26 of the two elements superposed, and this relationship is held by engagement of the key 30 (FIG. 1) in the grooves to inhibit mutual rotation while allowing axial sliding between the elements. In this keyed configuration the apertures 24 of the slider element, which are essentially circular in individual plan view and have corresponding transverse dimensions to the housing element apertures 13, can be aligned in superposed relationship with the aperture 13 over a range of sliding adjustment by virtue of the elongated shape of the latter apertures. The key 30 is, as presently illustrated, a rod of circular section deployed as a sliding fit between the relevant grooves, but it can be formed as a bolt threadably engageable with the housing element or some other manner as to secure the elements 10 and 20.

The rotation element 40 (FIGS. 9 to 11) comprises a spherical body 41 having a diametral bore 42 therethrough to receive the bone pin 110 in sliding engagement. The body 41 is additionally formed radially, in diametral opposed relation perpendicular to the bore 42, with a pocket 43 and a projecting stud 44. The pocket communicates with the bore 42 and is of uniform circular cross-sectional shape except at its inner end where it is convergently tapered to form a seat for a roller in the form of a ball bearing 50 (FIG. 1).

Remaining component parts of the clamp of FIGS. 1 and 2 are of relatively simple structural form shown, like the key 30 and ball 50, only in these figures. These parts are the locking screw 60, thrust ring 70, and locking ring 80, and they together form the locking mechanism for the clamp.

The screw 60 is seen to be threadably engagement with the bore 22 of the slide element 20, the screw having a hexagonal recess or other formation at its trailing end for co-operation with a driving tool, and a spherical concavity at its leading end to engage the rotation element and ball.

The thrust ring 70 is an annular member dimensioned for coaxial sliding enegagement in the counterbore 23 of the slide element 20. The outer edges of this element are each chamfered, and at least one inner edge is also chamfered or spherically relieved to form a seat for the rotation element 40 as seen in FIG. 1.

The locking ring 80 is a part-annular spring member of circular section, that is to say, a circlip, dimensioned to seat in the circumferential groove 27 in the slide element.

Assembly of the clamp of FIGS. 1 and 2 is largely self-evident from these figures. The screw is engaged with the slide element, the ball is located in the rotation element pocket, the rotation element is positioned in the slide element with the ball adjacent the screw, the thrust ring is slid into the slide element to seat against the rotation element while encompassing the stud of the latter, the locking ring is snapped into its groove in the slide element to hold the thrust ring, rotation element and ball in place, and the slide element is engaged and keyed with the housing element.

Locking of this assembly is effected by driving the screw into the slide element. The force of this action is transmitted through the ball and rotation element to the thrust member, and this last member acts in turn to expand the locking ring and the axially-slotted end portion of the slide member to lock the latter within the housing element. The rotation element is, at the same time, of course, locked against the thrust member, and the ball is also urged against the pin to indent and lock the same in the rotation element.

Unlocking of the clamp by slight withdrawal of the screw from the slide member allows adjustment of the pin position. The pin can be adjusted axially of the clamp by corresponding movement of the slide element in the housing element within the limits determined by the elongate shape of the housing apertures relative to the slide apertures. Also the pin can be adjusted independently in azimuth and zenith by movement of the rotation element, the extent of these adjustments being determined by the shaping of the housing and slide element apertures through which the pin passes and/or by the central space of the thrust ring within which the rotation element stud can move correspondingly with the pin.

A factor to note in connection with these locking and adjustment actions is that the ball and its pocket must be dimensioned such that the former can project from each end of the latter in all positions of adjustment in zenith to allow engagement with both the screw when tightened and the pin when in use.

Considering now FIGS. 12 and 17 of the drawings: these show, as indicated above, a subsequently developed alternative rotation element of two-part construction. One of these parts, denoted 170, (FIGS 12 to 14) is in fact integrated with the thrust ring, the common annular member being denoted at 70, as in FIG. 1, and being axially extended from one side by like walls 171 equally spaced in parallel manner about an axial diametral plane of the member. The other part (FIGS. 15 to 17) is denoted at 140 and is derived from the previous rotation element 40 by reducing the same to a disc-form body 141 symmetrical about the bore 42 and pocket 43, the stud 44 being replaced by a sectoral slot 142 in the plane of symmetry and communicating with the bore.

In use of this alternative element, the disc-form part 140 is located, slotted edge first, between the walls of the other part 170 to seat on the thrust ring portion of the latter, with this last portion being located as before in the slide element to position the pocket, plus an associated ball, adjacent the screw. Locking is effected in essentially the same manner, except that locking of the pin will involve contraction of the slotted portion of the part 140 therearound by reaction against the thrust ring. In adjustment, variation in azimuth will involve rotation of the part 170 together with the part 140 carried therein, while variation in zenith will involve only rotation of the part 140 within the part 170.

Turning to the remaining figures of the drawings: these show a further developed form of clamp which is presently preferred. This form has a two-part rotation element generally similar to that just described, but does not employ a ball bearing. It is now considered that the use of a ball such as 50 in the thrust transmission as first conceived during development of the invention can cause indentation of the locking screw as well as the pin and this may, at least in time, lead to a localised deformation of the screw which disturbs attainment of a desired rotational adjustment.

Further differences seen in this preferred form are found in the disc part denoted 240 (FIG. 18 and 19) employed to afford adjustment in zenith. This part is similar to that, 140, already described in being slotted to allow locking by contraction about the pin, but differs in its slotting. In this case there are a pair of slots 241 equally spaced from the diametral plane of symmetry passing axially through the bore 42 and the circumferential face of the disc, these slots opening in opposed manner into the last-mentioned face to assume a skew-symmetrical relationship as seen in FIG. 18. The slots 241 are enlarged at their inner ends, as by transverse bores 242 through the disc, to distribute the stresses which arise from contraction, and a similar formation can be employed for appropriate ones of the slots 25 in the slide element 20. Also the bore 42 is axially grooved at 243 to enhance its grip on a pin when contracted therearound.

Figure 20:
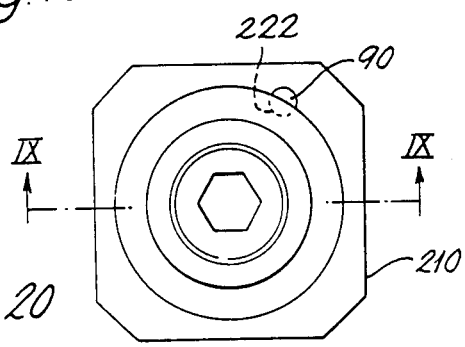
Figure 21:
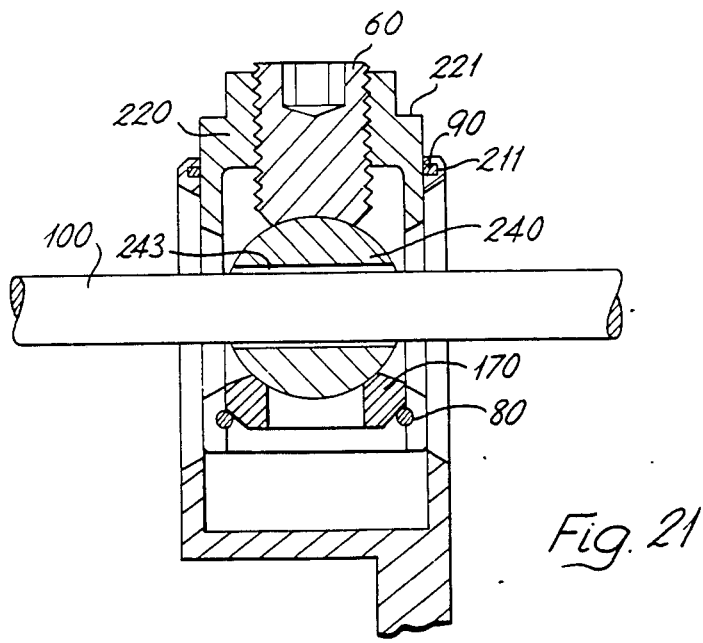

Differences are also found in the housing and slide elements respectively denoted 210 and 220 in their modified forms (FIGS. 20 and 21). The housing element has the bore of its end portion 12 formed adjacent its mouth with a circumferential groove 211. The slide element has its threaded screw-receiving end stepped down through a shoulder 221 to a reduced outside diameter and, at the same time, the axial groove 222 replacing previous groove 26 stops short of the ends of the slide element body. In assembly, a key 30 of length not greater than groove 222 is seated in that groove and the slide element slidably keyed into the housing element, whereafter, with the shoulder 221 located below the groove 222, a retaining ring of circlip form is sprung into the groove. The result is that the slide element can slide in the housing as required, but it cannot become accidentally disengaged because the key 30 is trapped by the retaining ring 90.

While the invention has been described with more particular reference to the illustrated embodiments, it will be appreciated from the variations therebetween that modification is possible in other respects within the scope of the initial more generalised discussion.

Variation is also possible in respect of the general usage of the presently proposed clamp. As so far described reference has been made to U.S. Pat. No. 4,271,832 in connection with such usage. However, the clamps of that patent are additionally useful in accordance with Pat. Application Ser. No. 404,498 filed Aug. 2, 1982 whereby an external orthopaedic fracture fixation apparatus is adapted to allow controlled relative movement between bone pins on respectively opposite sides of a fracture, and the same further application is equally possible with the presently proposed clamp. Also, it is not essential that the present clamp co-operate directly with a bone pin passing therethrough: another form of external orthopaedic fracture fixation apparatus employs adjustable clamps individually to secure to a support a pin which is connected in turn to a multiple clamp for holding a plurality of bone pins in a fixed parallel array, and the present clamp is well suited to such use.

I claim:

1. For an external orthopaedic fracture fixation apparatus, a clamp comprising:
   a housing element having one end portion hollowed to serve as a cylinder; said portion having a pair of diametrally opposed apertures for passage of a pin therethrough, and said apertures being elongated axially of said cylinder;
   a slide element of generally open-ended tubular form located in keyed manner in said housing element cylinder for non-rotatable axially reciprocal movement therein as a piston, said slide element having a pair of diametrally opposed apertures aligned with, but axially shorter than, those of said housing element for receipt of the pin, said slide element being axially slotted through one end portion thereof, and said slide element having an inward projection circumferentially around said one end portion;
   an annular thrust member coaxially located in said slide element to seat on said inward projection;
   a rotation element rotatably located in said slide element to seat on said thrust member oppositely from said projection, said rotation element having a bore therethrough aligned with said housing element apertures and said sliding element apertures for receipt of the pin, and said rotation element having at least one slot extending therethrough from its exterior to its bore; and
   a locking screw axially threadably engaged in said slide element oppositely from said one end portion, said screw being operably movable into said slide element to engage said rotation element to act on said thrust member thereby to urge said thrust member against said projection and to lock said slide element by expansion in said housing element, and simultaneously to lock said rotation element and a pin passing therethrough by compaction of said rotation element between said screw and thrust members.

2. A clamp according to claim 1 wherein said thrust member has an annular portion axially aligned with said screw and includes two diametrally spaced walls projecting axially from one side thereof, and said rotation element includes a part of disc form diametrally bored for passage of said pin therethrough, said disc being located edgeways between said thrust member walls, said thrust member and said disc being rotatable together in said slide element to afford adjustment of said bore in azimuth and zenith, said disc being independently rotatable in said thrust member to afford adjustment of said bore in zenith.

3. A clamp according to claim 1 wherein said rotation element includes a part having the bore therethrough, said part having a pocket transversely communicating its external surface with its bore, and a roller seated in said pocket, said screw acting on said rotation element by way of said roller.

4. A clamp according to claim 3 wherein said rotation element part is a substantially spherical body rotatable in said slide element to afford both azimuth and zenith adjustment for the bore.

5. A clamp according to claim 1 wherein said rotation element includes a part having the bore therethrough, said part being of a split form compactable by movement of said screw.

* * * * *